(12) United States Patent
Klint et al.

(10) Patent No.: US 7,654,986 B2
(45) Date of Patent: Feb. 2, 2010

(54) NEEDLE MOUNTING SYSTEM AND A METHOD FOR MOUNTING A NEEDLE ASSEMBLY

(75) Inventors: Henrik Sonderskov Klint, Lyngby (DK); Jim Radmer, Fredensborg (DK); Jorgen K. Smedegaard, Frederiksberg (DK); Jan Frank Nielsen, Lyngby (DK); Peter Moller Jensen, Horsholm (DK); Jens Moller Jensen, Copenhagen K (DK)

(73) Assignee: Novo Nordisk A/S, Bagsvaerd (DE)

( * ) Notice: Subject to any disclaimer, the term of this patent is extended or adjusted under 35 U.S.C. 154(b) by 378 days.

(21) Appl. No.: 10/609,744

(22) Filed: Jun. 30, 2003

(65) Prior Publication Data
US 2004/0054336 A1    Mar. 18, 2004

Related U.S. Application Data

(60) Provisional application No. 60/394,083, filed on Jul. 3, 2002.

(30) Foreign Application Priority Data

Aug. 1, 2002    (DK) .......................... PA 2002 01169

(51) Int. Cl.
*A61M 5/00*    (2006.01)
(52) U.S. Cl. ........................ 604/240; 604/241; 604/242; 604/243
(58) Field of Classification Search ......... 604/240–243, 604/93.01, 181, 187, 188, 272, 533–535, 604/538
See application file for complete search history.

(56) References Cited

U.S. PATENT DOCUMENTS

| | | | |
|---|---|---|---|
| 1,757,680 A | 5/1930 | Neil | |
| 1,793,068 A | 2/1931 | Dickinson | |
| 2,828,743 A | 4/1958 | Ashkenaz et al. | |
| 2,834,346 A | 5/1958 | Adams | |
| 2,842,126 A | 7/1958 | Brown | |
| 2,894,509 A | 7/1959 | Bednarz | |

(Continued)

FOREIGN PATENT DOCUMENTS

CH        332340        * 10/1958

(Continued)

OTHER PUBLICATIONS

Machine English language translation of FR 2,623,403 (previously submitted).

(Continued)

*Primary Examiner*—Kevin C Sirmons
*Assistant Examiner*—Laura C Schell
(74) *Attorney, Agent, or Firm*—Wesley A. Nicolas; Reza Green; Marc A. Began

(57) ABSTRACT

A needle mounting system and methods for mounting a needle assembly on a needle mount are disclosed. The needle mounting system includes a needle hub having protrusions extending radially inward. A needle mount has a plurality of slots to receive the protrusions. The slots have a first portion that defines a passageway substantially parallel to a longitudinal axis of the needle mount and a second portion substantially perpendicular to the axis. The needle hub and mount provide a method wherein a needle assembly may be mounted on an injection device without completely rotating the needle hub relative to the needle mount.

12 Claims, 8 Drawing Sheets

U.S. PATENT DOCUMENTS

| | | | |
|---|---|---|---|
| 3,278,357 A | 10/1966 | Gettig et al. | |
| 4,340,148 A | 7/1982 | Beckham | |
| 4,568,336 A | 2/1986 | Cooper | |
| 4,624,393 A | 11/1986 | Lopez | |
| 5,019,045 A * | 5/1991 | Lee | 604/110 |
| 5,205,833 A | 4/1993 | Harsh et al. | |
| 5,273,543 A * | 12/1993 | Bell et al. | 604/110 |
| 5,279,586 A * | 1/1994 | Balkwill | 604/207 |
| 5,611,786 A | 3/1997 | Kirchhofer et al. | |
| 5,693,027 A | 12/1997 | Hansen et al. | 604/232 |
| 6,126,646 A | 10/2000 | Hansen et al. | 604/256 |
| 6,312,413 B1 | 11/2001 | Jensen et al. | 604/232 |
| 6,346,094 B2 | 2/2002 | West et al. | 604/241 |
| 6,454,745 B1 * | 9/2002 | Donnan et al. | 604/181 |

FOREIGN PATENT DOCUMENTS

| | | |
|---|---|---|
| EP | 55859 | 7/1982 |
| EP | 1216719 | 6/2002 |
| FR | 2623403 | 11/1987 |
| GB | 594366 | 11/1947 |
| GB | 737676 | 9/1955 |
| WO | 96/11028 | 4/1996 |
| WO | 02/11798 | 2/2002 |

OTHER PUBLICATIONS

Certified English Language translation of CH 332340.
Office Action from the Chinese Patent Office dated Dec. 5, 2008 in Application No. 03815651.2.
Office Action from the Chinese Patent Office dated Mar. 9, 2007 in Application No. 03815651.2.
Office Action from the Russian Patent Office dated Apr. 9, 2007 in Application No. 2005102605.
Search Report in International Patent Application No. PCT/DK03/00451 dated Sep. 23, 2003.
International Preliminary Examination Report from the European Patent Office in Application No. 03 762 466.5 dated Jun. 27, 2005.
European Search Report from the European Patent Office in Application No. 06121820.2 dated Sep. 12, 2007.
Extended European Search Report from the European Patent Office in Application No. 06121820.2 dated Nov. 22, 2007.
Machine English language translation of FR 2,623,403.
Penfine® universal click™ 8mm needle product box having an expiration date of Nov. 2005.
Clickfine® universal needle instructions (date unknown).
Clickfine® universal needle brochure (date unknown).

* cited by examiner

NEEDLE MOUNTING SYSTEM AND A METHOD FOR MOUNTING A NEEDLE ASSEMBLY

CROSS REFERENCE TO RELATED APPLICATIONS

This application claims priority under 35 U.S.C. 119 of Danish application no. PA 2002 01169 filed Aug. 1, 2002, and U.S. provisional application No. 60/394,083 filed Jul. 3, 2002, the contents of which are fully incorporated herein by reference.

THE TECHNICAL FIELD OF THE INVENTION

The present invention relates generally to injection devices and, in particular, provides methods and systems for mounting a needle to an injection device or to an ampoule that my be mounted in the injection device.

DESCRIPTION OF RELATED ART

Injection devices, also referred to as dosers, have greatly improved the lives of patients who must self-adminster drugs and biological agents. Dosers may take many forms, including simple disposable devices that are little more than an ampoule with an injection means or they may be highly sophisticated instruments with numerous functions. Regardless of their form, they have proven to be great aids in assisting patients to seif-adminster injectable drugs and biological agents. They also greatly assist care givers in administering injectable medicines to those incapable of performing self-injections.

In particular, pen-style injection devices, have proven to be an accurate, convenient, and often discrete, way to administer drugs and biological agents, such as insulin. Modern devices have become more sophisticated and often include diverse and robust functions, such as memories for remembering time and amount of last dose, as well as, in the case of insulin devices, blood glucose monitors. While pen-style dosers are typically cylindrically shaped with needles protruding from the most distal portion of one end of the device, some of the more modern and/or sophisticated dosers have other shapes with the needle no longer protruding from the most distal part of an end of the device. (See e.g., Innovo® and InnoLet® from Novo Nordisk A/S Bagsvaerd Denmark).

Typically, injection devices use a pre-filled cartridge containing the medication of interest. The cartridge may be an integral part of the doser or it may comprise an ampoule having a membrane at one. See U.S. Pat. No. 6,312,413 to Jensen et. al, which is hereby incorporated by reference. Often the end of the ampoule having the membrane is fitted with a needle mount. The needle mount usually comprises a threaded mounting surface to allow a needle assembly, such as a needle and hub assembly, to be screwed on. The needle mount may be an integral part of the ampoule or may be a separate adapter top (see U.S. Pat. Nos. 5,693,027 and 6,126, 646, which are hereby incorporated by reference) that is mounted to the ampoule. Of course, some dosers have needle mounts that are integral parts of the doser.

In the typical injection device where the needle mount is not part of the doser, the end of the ampoule having the needle mount protrudes from the injection device. Where the needle mount is part of the doser, the needle mount is usually disposed on an outer end of the doser. In either embodiment, the needle hub is then screwed onto the needle mount. One disadvantage of the prior art needle mounting systems is that they require the patient to screw the needle hub onto the end of the ampoule, or the doser, by turning the needle relative to the device several times. For patients with dexterity problems, this is inconvenient. Moreover, it is often desirable to store needles for the injection devices in a magazine. Often many newer generation injection devices are not cylindrical and in many new devices, other parts of the device extend past the needle mount making it impossible to mount the needle on the injection device without first removing it from the magazine.

SUMMARY OF THE INVENTION

The present invention provides systems and methods for mounting needle assemblies to injection devices and/or ampoules. In some, but not necessarily all embodiments, the system and method of the present invention allows a needle and hub assembly to be mounted on an ampoule and/or injection device without having to rotate completely the needle hub assembly relative to the injection device. In one embodiment of the present invention, a needle assembly is comprised of a needle mounted in a hub. The needle assembly also includes a means for mounting the hub to a needle mount with only a partial rotation of the needle hub relative to the mount. In an other embodiment of the present invention, a needle mount for mounting the needle assembly is comprised of an outer wall and a mounting means for affixing the needle assembly to a top end of the outer wall. In some embodiments, the means provides for completely securing the needle assembly to the needle mount with only a partial rotation of the needle mount. In some embodiments, the needle mount includes a means for aligning the needle assembly on the mounting means. The needle mount and needle assemblies of the present invention, when combined, make up a needle mounting system. The system, or its components, may also include a means for tactilely or audibly determining when the needle assembly is securely mounted on the needle mount.

At least one embodiment of the present invention includes a needle assembly that is comprised of a needle mounted to a hub having an interior wall. In this embodiment, a plurality of protrusions extends radially inward from the wall of the hub. Typically, the hub wall is cylindrical. A needle mount for use with the present invention, may in at least one embodiment, include a structure having a cylindrical outer wall. A plurality of grooves is disposed on the outer wall. The grooves begin at the top of the wall and contain at least two portions: a first portion that defines a passageway that is substantially parallel to the cylindrical axis of the outer wall, and a second portion that is oriented at an angle to the first portion. Of course, the present invention may be embodied in structures wherein the grooves are disposed inside the hub of the needle mount and the protrusions are disposed on an outer surface of the needle mount.

In at least one embodiment of the present invention, the needle assembly is completely mounted on an injection device with only a partial rotation of the needle assembly relative to the injection device. (Those skilled in the art will recognize that rotation of the needle assembly relative to the injection device may be accomplished by holding the device stationary and rotating the needle assembly or by holding the needle assembly stationary and rotating the device or by a combination of these steps). In some embodiments, the needle is mounted on an ampoule that is mounted in the injection device.

The present invention therefore provides a method for mounting needles to injection devices. The method may be useful in mounting needles stored in magazines and is particularly useful for injection devices that have a portion that extends past the needle mount. In one embodiment, the injection device is partially inserted into a magazine holding needle assemblies. The injection device is rotated relative to the magazine by less than a full revolution and is then removed with the needle assembly attached thereto. In some embodiments no or minimal rotation is required.

In other embodiments of the present invention, the needle assembly may include a cylindrical hub that has a needle mounted thereon. The hub may have an internal cylindrical element with an outside cylindrical wall that faces the hub's inside cylindrical wall. A plurality of protrusions may extend radially outward from the internal cylindrical element. A corresponding needle mount may be used. The needle mount, in one embodiment, may include a plurality of locking elements arranged on an interior cylindrical surface (e.g., a wall) of the needle mount to form first passageways that are substantially parallel to the cylindrical axis of the needle hub. In some embodiments, the locking elements are disposed on a ring that is part of the interior surface or that is attached to, or part of, an inside wall of the needle mount.

Further the protrusions could be sized to fit between threads of a standard ampoule adapter top. The protrusions arranged on the inner hub wall and aligned between the threads of a standard adapter top would allow the needle assembly to be screwed onto the adapter top in a traditional manner.

DETAILED DESCRIPTION OF THE INVENTION

Figure 1:
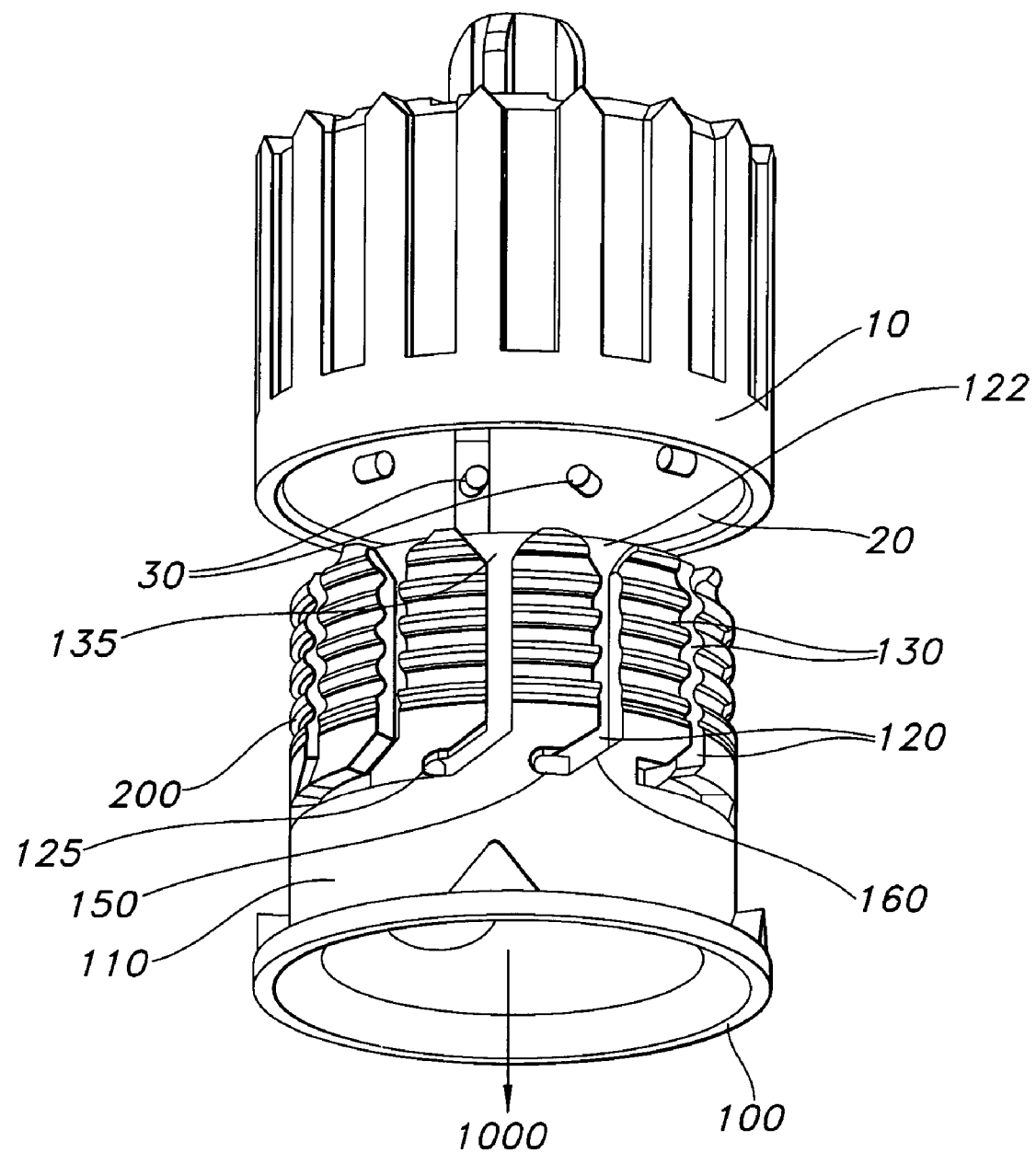
FIG. 1 is a three-dimensional view of a needle hub and needle mount according to one embodiment of the present invention.

The present invention provides for systems and methods for attaching needle hub assemblies to ampoules and injection devices. Typically, a needle hub assembly comprises a needle 510 mounted to a hub 500 (see e.g. FIG. 3). As is shown in FIG. 1, a needle hub 10 may be generally cylindrically shaped and have an interior wall surface 20. In one embodiment of the present invention, a plurality of protrusions 30 extends radially inward from the interior surface 20.

Figure 2:
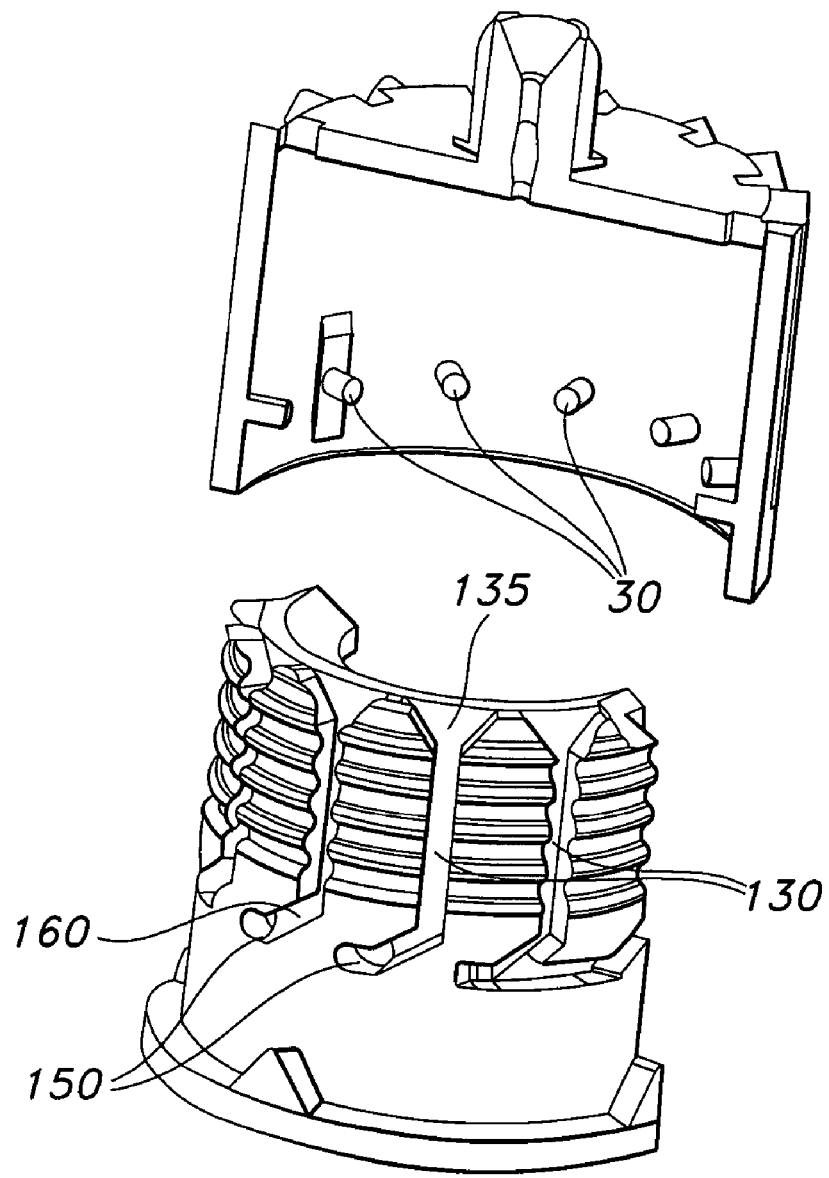
FIG. 2 is a cut-away view of the needle mount and needle hub shown in FIG. 1.

A needle mount 100 is designed to accept the needle hub 10. (See e.g. FIG. 1). As is shown in FIGS. 1 and 2, the needle mount 100 may be generally cylindrically shaped and have an exterior wall surface 110. A plurality of grooves or slots 120 are disposed in the exterior surface 110. The grooves 120 have a first end 122 and a second end 125. The grooves 120 have a first portion 130 that defines a passageway that is generally parallel to the cylindrical axis 1000 of the needle mount 100. While the first portion of the groove 130 is shown in the drawings as having a rectangular portion, the exact shape of the groove is not critical so long as it allows the protrusions 30 on the needle hub to move in a direction parallel to the cylindrical axis 1000. Thus, while the groove may have walls that are not necessarily parallel to the cylindrical axis 1000, the groove may still be said to be parallel to the cylindrical axis if it allows the protrusions 30 to move in a direction parallel to the cylindrical axis. The first portion of the grooves 130 may have width that is wider than the remainder of the first portion or the remainder of the groove 130. In embodiments where the groove has walls that are not parallel to the cylindrical axis 1000, the width of the first portion of the groove 130 may be the average width for the first portion of the groove 130.

The first portion 130 may have an entrance 135 that has a width dimension that is greater than the average width of the first portion or is wider than the average width of the entire groove 120. The entrance 135 may act as an alignment means for aligning the needle hub so that the protrusions will enter the groove 120. In most embodiments, but not all, the entrance width is wider than any other point in the groove 120. Typically the width of the groove narrows as the groove is traversed away from the entrance 135. As is shown, the groove may reach a constant width at some distance from the opening. In some embodiments the width of the first portion 130 is widest at the entrance 135 and continues to narrow over the length of the first portion 130. The grooves also have a second portion 150 that is either perpendicular to the cylindrical axis 1000, or lies at angle to the first portion 130. In some embodiments of the present invention the second portion 150 may be comprised of only one surface that is generally perpendicular to the cylindrical axis of the needle mount. Thus, the second portion of the groove 150 need not be a slot having two sides, but needs only one side to prevent protrusions on the needle hub from moving toward the outer end of the needle mount. As shown in FIG. 1, the grooves 120 may also have a third portion 160 that is oriented at an angle to the first portion 130 and the second portion 150.

Figure 7:
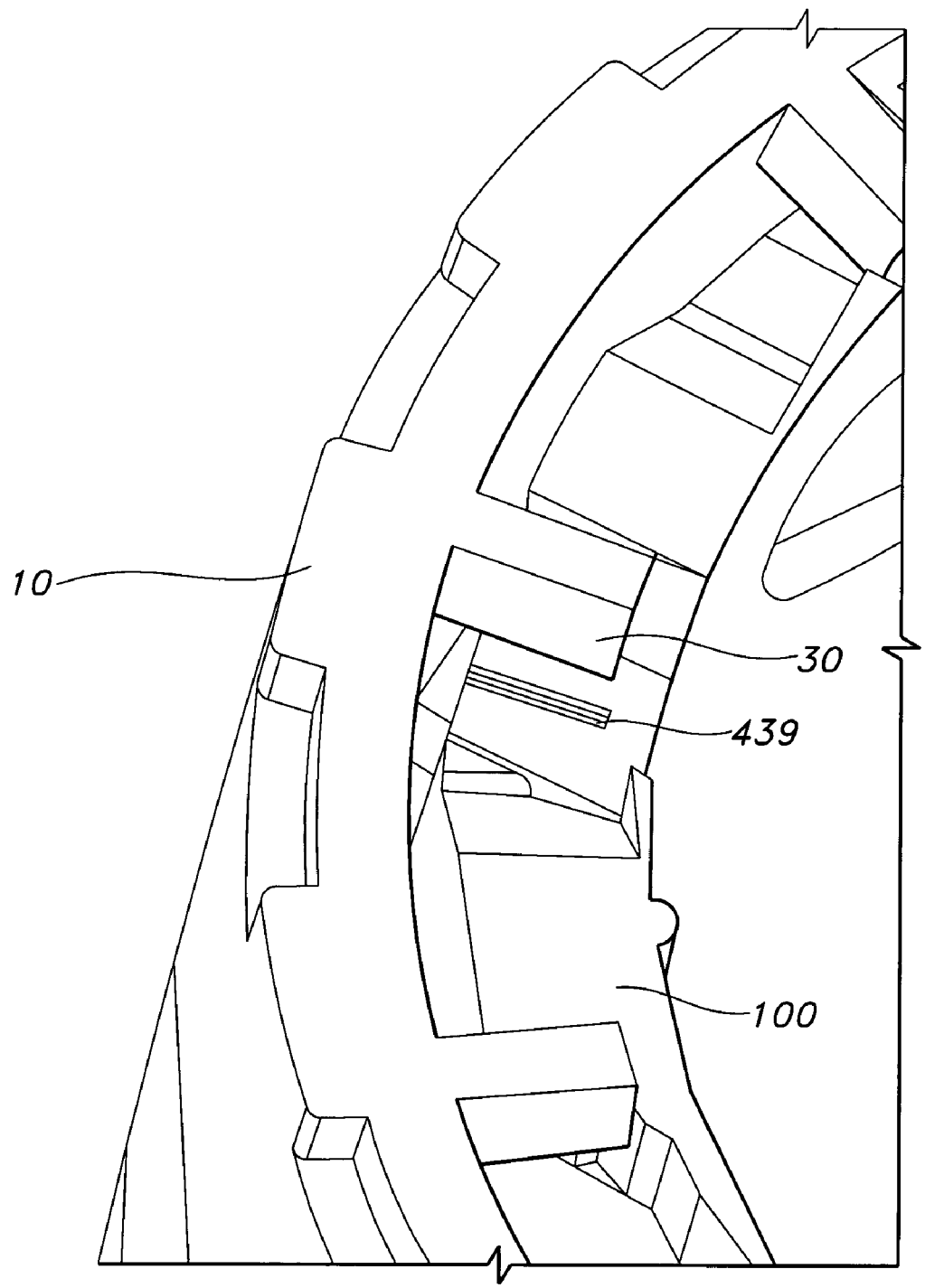
FIG. 7 is a cut through view of the needle mount and needle hub illustrating one embodiment of the present invention for tacitly determining whether the needle hub is securely mounted on the needle mount.

In some embodiments of the present invention a means for tacitly determining whether the needle assembly is securely fixed to the hub is provided. This may be accomplished in numerous different ways, including providing a small projection(s) 439 at the side or in the bottom of the second portion of the grooves 120. (See e.g. FIG. 7). The protrusions 30 have to overcome the projections 439 before the needle is fixed. The deformation of the projections may cause a tacitly feel or a sound, such as a clicking sound. Thus, in some embodiments of the present invention, the needle mounting system can be designed so that the needle hub and the needle mount generate a clicking sound when the needle is securely placed on the mount. When the hub is to be remounted from injection device the oblique tactile protrusions can be more sharp at their ends, so that hub is better fixed during injection and handling etc. This also makes it possible for the patient to keep the needle for more injection.

One advantage of the present invention is that the needle mount, may be equipped with standard threads 200 on its exterior surface. (See FIG. 1). The grooves 120 may be cut into the standard threads 200. This allows the needle mount 100 to accept not only needle hubs of the present invention, but also standard, threaded needle-hub assemblies.

While FIG. 1 shows the grooves on the needle mount and the protrusions on the needle hub, the present invention may be configured with the grooves located on the interior surface of the needle hub and the protrusions extending outward from the exterior wall of the needle mount. In some embodiments it may be advantageous to size and shape the protrusions so that they fit between standard threads used with existing needle hubs. The protrusions may then be arranged on the exterior wall of the needle mount to allow not only needle hub assemblies having grooves in their interior wall to be attached, but also standard, threaded needle hubs.

The present invention may take numerous other forms, including—but not limited to—that shown in FIGS. 3-6. As is shown in FIGS. 3-6. the needle hub assembly 500 has a needle 510 mounted thereto. The needle hub 550 may be generally cylindrically shaped and has an interior wall surface 600 and a closed top end 610. The closed top end 610 has an inside surface 620. A cylindrical member 650 protrudes from the inside surface 620 and has an outer surface 660. See FIG. 5. Protrusions 670 extend radially outward from the outer surface 660. The protrusions may take various forms and shapes, including the triangular prism shape shown in the drawings.

Figure 3:
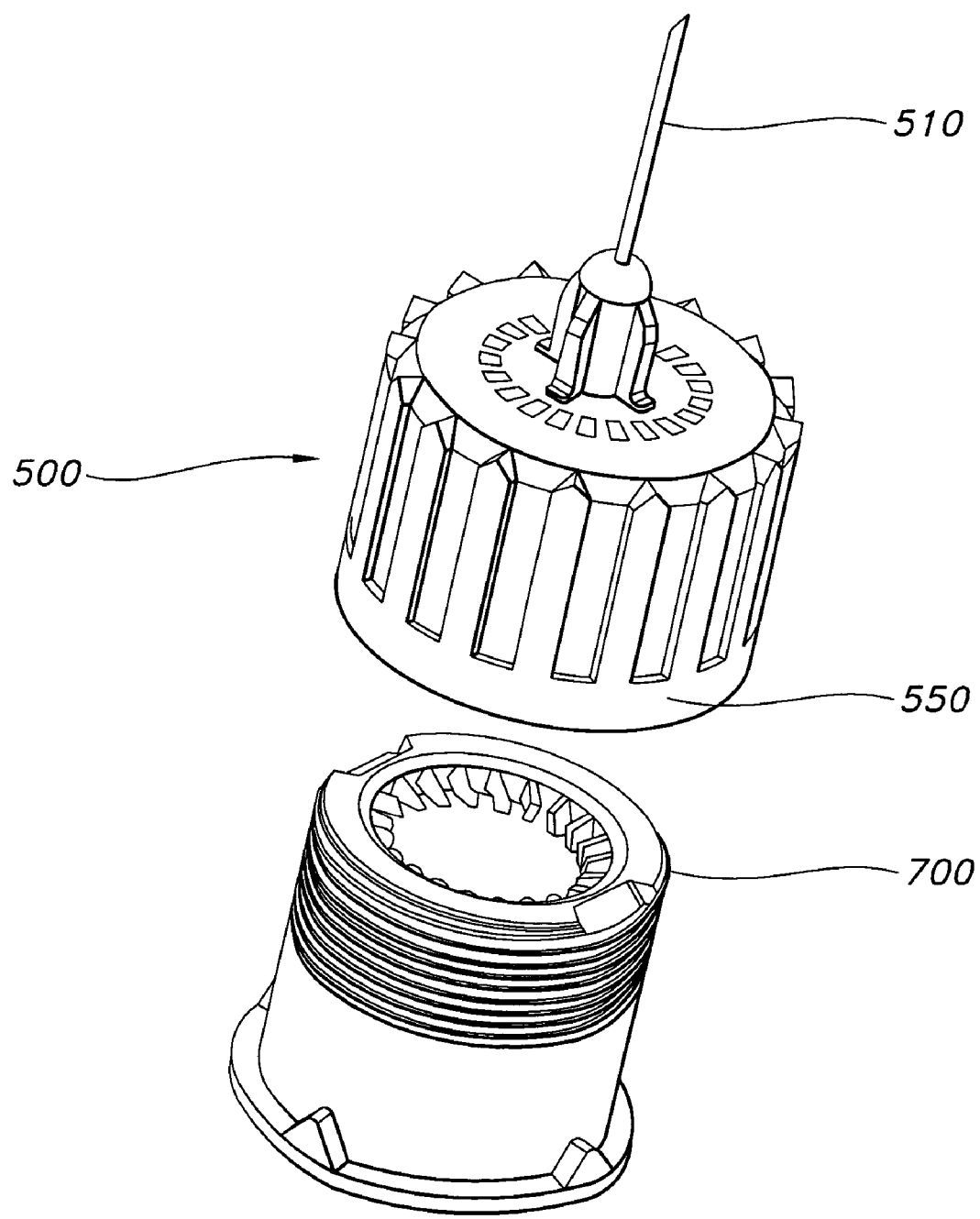
FIG. 3 is a three-dimensional view of a needle assembly and needle mount according to a second embodiment of the present invention.
Figure 4:
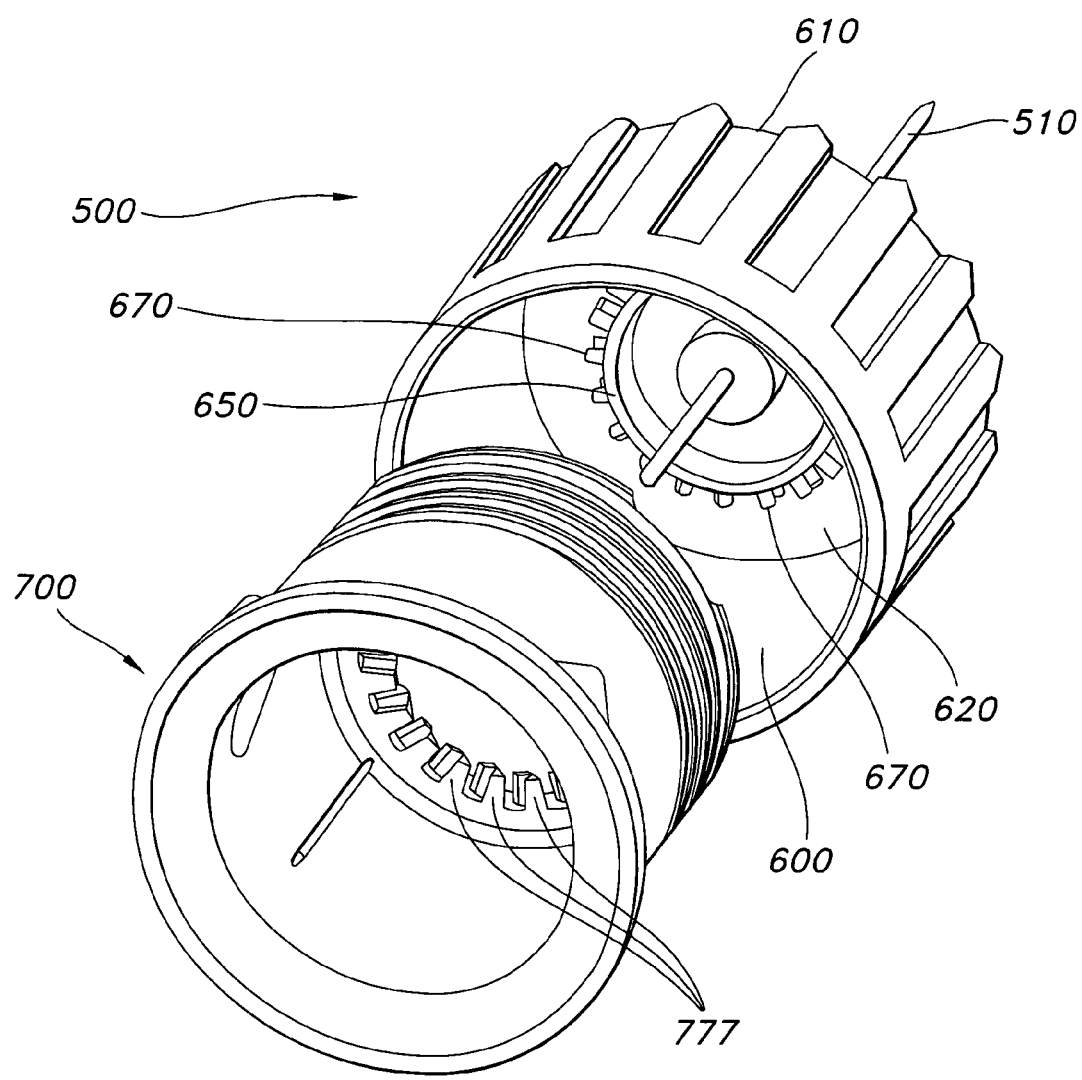
FIG. 4 illustrates the embodiment of FIG. 3 when viewed from below.
Figure 5:
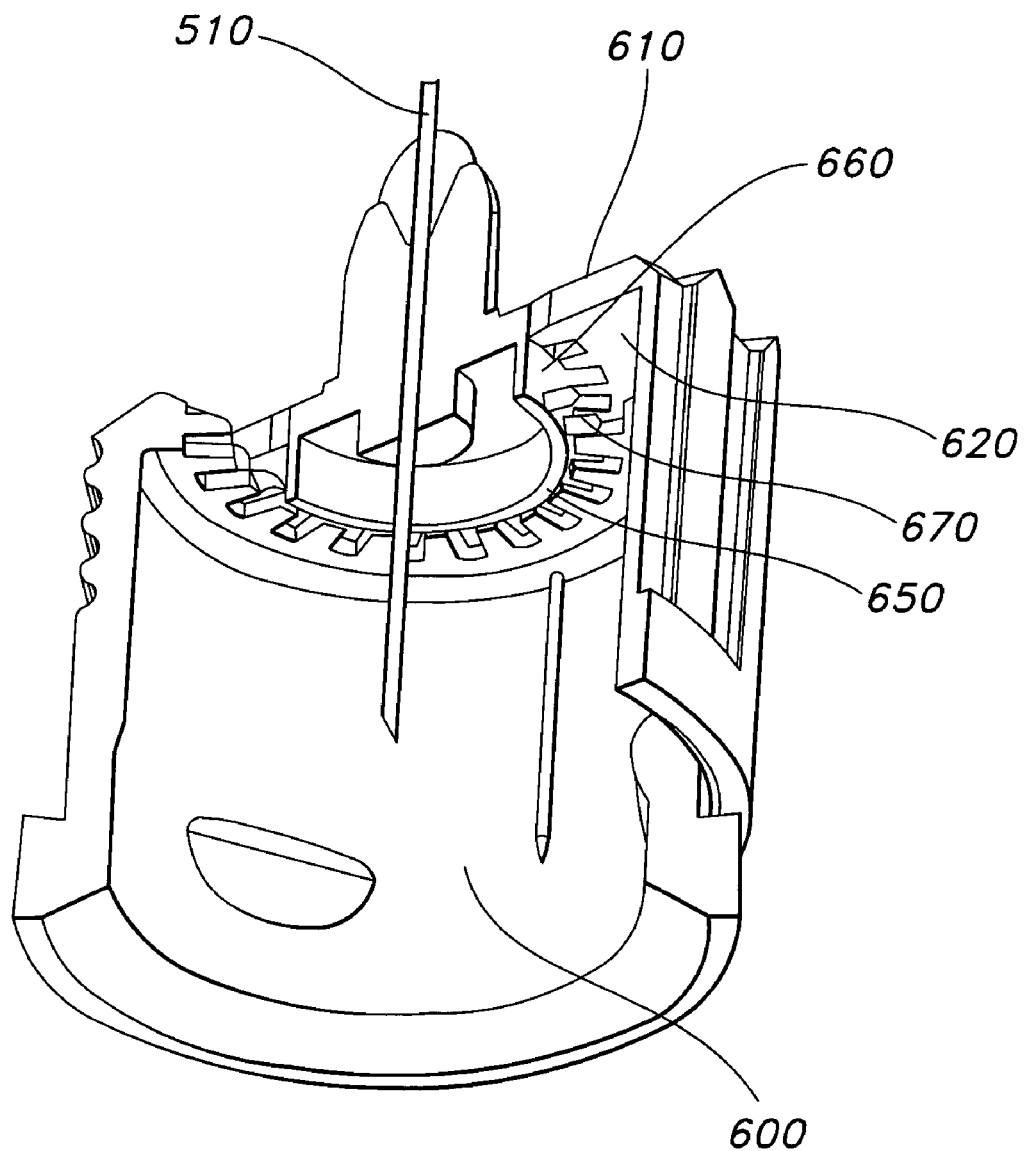
FIG. 5 is a cut-way view of the needle assembly of FIGS. 3-4.
Figure 6:
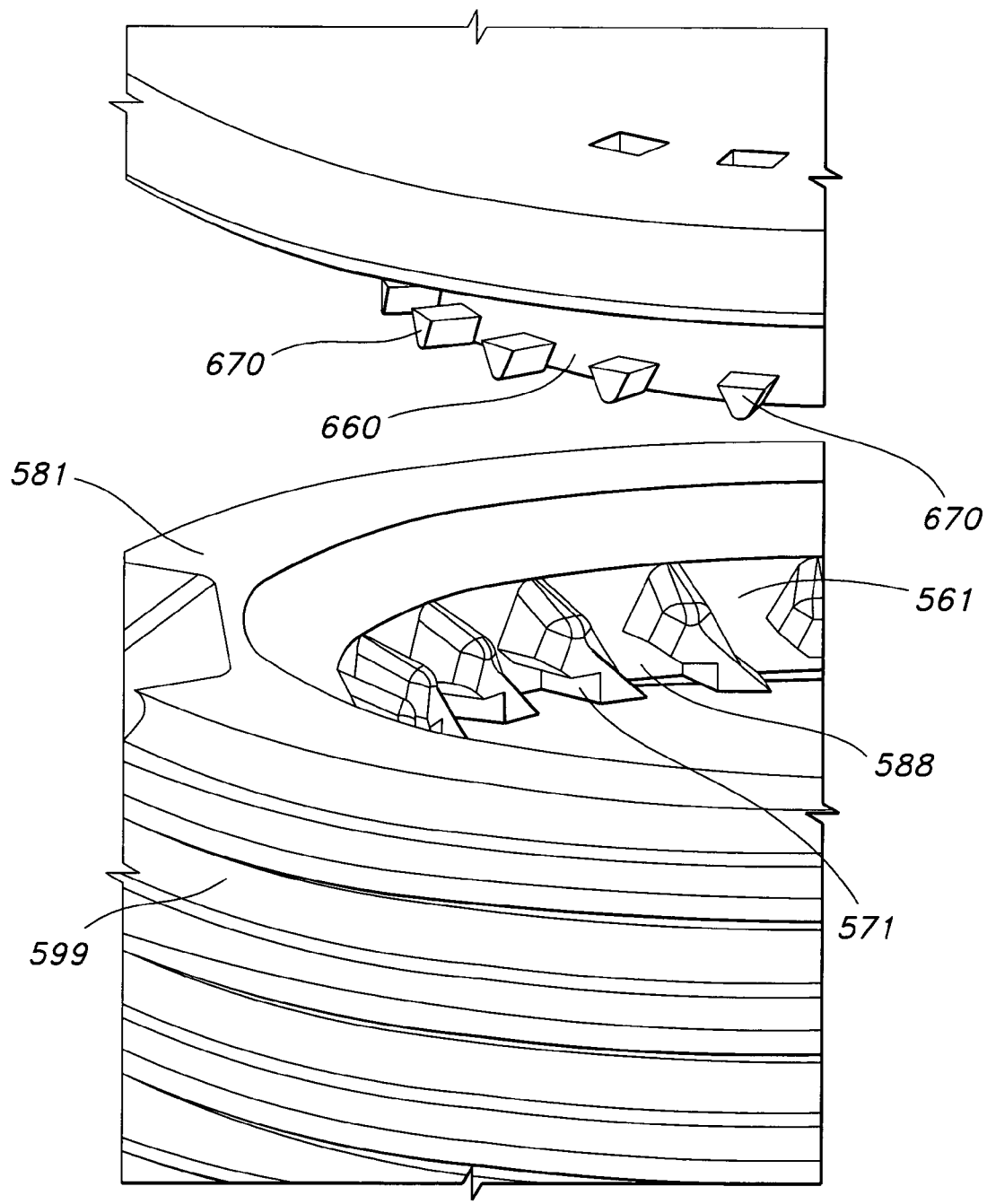
FIG. 6 is an enlarged view of the needle assembly mounting means of the embodiment shown in FIGS. 3-5.

The needle hub assembly shown in FIGS. 3-5 may be used with a modified needle mount, 700. As is shown in FIGS. 3-6, the needle mount 700 may be generally cylindrically shaped and have a top end, an interior surface, an exterior surface, and a plurality of locking elements (which may be additional protrusions) extending from the interior surface inward. The locking elements may be arranged to form passageways for the protrusions 500 on the needle mount, thereby forming a plurality of grooves for accepting the protrusions from the needle hub assembly 500. As is shown in FIG. 6, the grooves may have a first portion 561 that defines a passageway that is generally parallel to the cylindrical axis of the needle mount, a second portion 571 that is perpendicular to the cylindrical axis and a third portion 588 that connects the second 571 and first portions 561. The first portion 561 may be widest at its opening and thus act as an alignment mechanism for the protrusions on the needle hub. The needle mount may have a mounting surface 581 on which a portion of the needle hub rests when the needle hub is mounted on the needle mount. The mounting surface may be a top edge of the top end of needle mount, or it may be the exterior wall surface 599 of the needle mount or both. The embodiment shown in FIGS. 2-4 also advantageously allows the outer surface of the needle mount to have threads so that standard prior-art needle hubs may be used with the improved needle mount of the present invention.

The present invention enables various methods for attaching a needle-hub assembly to an ampoule or injection device. For example, in one embodiment of the present invention, a needle mount is inserted into a needle hub, the needle hub is rotate relative to the needle mount less than one revolution—typically between 5 and 30 to 60 degrees. In some embodiments, a clicking noise or vibration or other tactile feedback will be provided to indicate that the needle is securely mounted to the hub. In some embodiments little rotation is necessary. In some embodiments, it is possible that no rotation is needed. The surface of the locking element 777 could simply force the hub to rotate upon insertion of the mount into the interior of the hub 500. In other embodiments, more rotation may be required.

Figure 8:
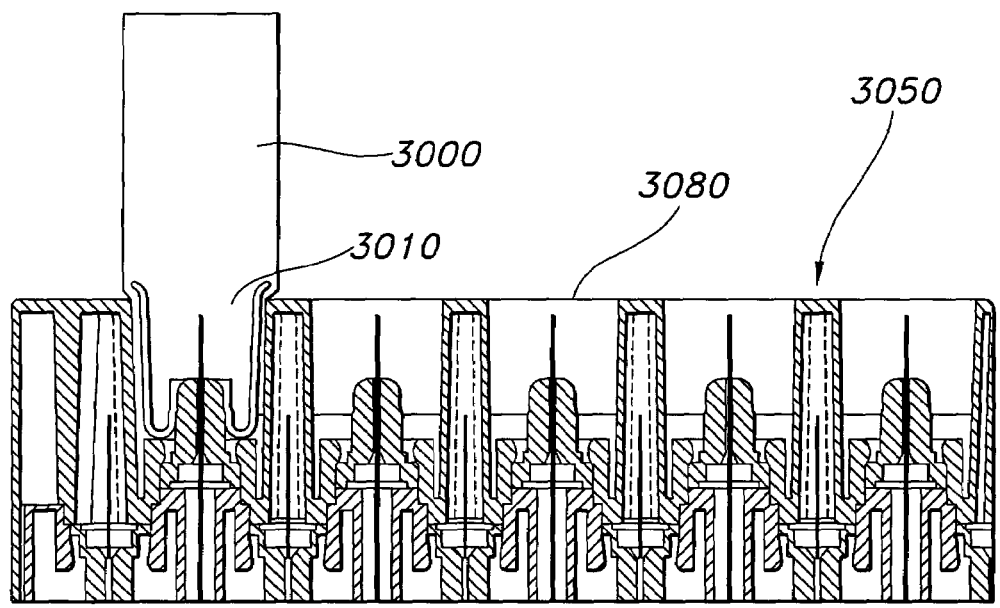
FIG. 8 is a side view of a magazine for storing needles that may be used in practicing the method steps of the present invention.
Figure 9:
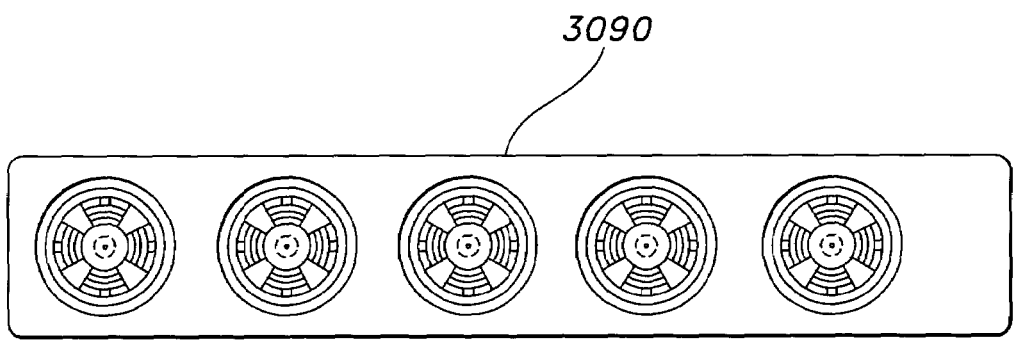
FIG. 9 is a top view of the magazine shown in FIG. 8.

Because the methods of mounting a needle hub to a needle mount do not require that the hub be rotated a full revolution relative to the mount (i.e. either the hub is rotated and the mount is held stationary or the mount is rotated and the hub is held stationary, or both are turned in opposite direction), the present invention enables and provides for methods of mounting needle-hub assemblies stored in magazines, similar to that shown in FIGS. 8 and 9, to injection devices where their shape would not allow the device to be rotated relative to the magazine by a full revolution. In one embodiment of the present invention, a portion of an injection device 3000, usually the portion containing a needle mount 3010, is inserted into a needle magazine 3050. The device 3000, without being rotated a full revolution is then removed with a needle fully attached to it. In some embodiments audible or tactile feedback is provided to indicate that the need is securely mounted to the device. In some embodiments, the portion of the device that is inserted into the magazine may be an end portion of an ampoule that extends from the device. Some methods of practicing the present invention may be performed using the needles are stored in a magazine having a flush surface 3070 and the needle and hub assemblies 3080 are located below the surface 3070, usually—but not necessarily—in recessed cavities 3090 (see FIG. 9).

The foregoing is a brief description of some exemplary embodiments of the present invention and is intended to be illustrative and not exhaustive of the present invention. Those of skill in the art will recognize the nature of language makes it impossible to capture the essence of all aspects of the present invention and unimportant and insubstantial substitutes for various elements are intended to be included within the scope of the invention as defined by the following claims.

We claim:

1. A needle mounting system for mounting and dismounting a needle assembly onto a needle mount of an injection device, comprising:

a needle assembly comprised of:

a hub that is attached to a needle, the hub having an interior wall, wherein the interior wall of the hub is cylindrical and comprises a plurality of protrusions extending radially inward from the interior cylindrical wall of the hub, a needle mount comprised of two separate coupling mechanisms comprising a first coupling mechanism and a second coupling mechanism, the needle mount comprising:

a cylindrical outer wall having a top end and threads disposed on the cylindrical outer wall, the first coupling mechanism comprising a plurality of grooves disposed in the cylindrical outer wall beginning at the top end of the cylindrical outer wall and defining a passageway that is generally parallel to a cylindrical axis of the cylindrical outer wall, and wherein at least one groove of the needle mount comprises a first portion and a second portion oriented at an angle to the first portion, wherein the first portion and second portion do not form a part of the second coupling mechanism and wherein the protrusions of the needle hub interact with the grooves to form a bayonet coupling, and the second coupling mechanism comprising threads disposed on the cylindrical outer wall are suitable for threadedly connecting and matingly fitting a conventional threaded needle assembly to the needle mount, thereby allowing either a threaded needle hub to be mounted or dismounted onto the needle mount via the second coupling mechanism, or a bayonet needle hub to be mounted or dismounted onto the needle mount via the first coupling mechanism.

2. The needle mounting system according to claim 1, wherein the angle between the first portion and the second portion is 90 degrees or less.

3. The needle mounting system according to claim 1, wherein the first portion of the groove is widest at the top end of the needle mount defining an entrance.

4. The needle mounting system according claim 1, wherein the protrusions comprise a circular surface.

5. The needle mounting system according to claim 1, further comprising a means for determining whether the needle hub is securely mounted on the needle mount.

6. The needle mounting system according to claim 1, wherein the needle mount is on an adapter top that is secured to an ampoule, or an injection device.

7. A needle mounting system for mounting and dismounting a needle assembly onto a needle mount of an injection device, comprising:
　　a needle assembly comprised of:
　　　　a hub that is attached to a needle, the hub having an interior wall, wherein the interior wall of the hub is cylindrical and comprises a plurality of protrusions extending radially inward from the interior cylindrical wall of the hub, and around the circumference on the interior wall of the hub,
　　a needle mount comprised of two separate coupling mechanisms comprising a first coupling mechanism and a second coupling mechanism, the needle mount comprising:
　　　　a cylindrical outer wall having a top end and threads disposed on the cylindrical outer wall,
　　　　the first coupling mechanism comprising a plurality of grooves disposed in the cylindrical outer wall beginning at the top end of the cylindrical outer wall and defining a passageway that is generally parallel to a cylindrical axis of the cylindrical outer wall, and wherein at least one groove of the needle mount comprises a first portion and a second portion oriented at an angle to the first portion, and wherein the protrusions of the needle hub interact with the grooves to form a bayonet coupling, and
　　　　the second coupling mechanism comprising threads disposed on the cylindrical outer wall are suitable for threadedly connecting and matingly fitting a conventional threaded needle assembly to the needle mount,
　　　　thereby allowing either a threaded needle hub to be mounted or dismounted onto the needle mount via the second coupling mechanism, or a bayonet needle hub to be mounted or dismounted onto the needle mount via the first coupling mechanism.

8. The needle mounting system according to claim 7, wherein the angle between the first portion and the second portion is 90 degrees or less.

9. The needle mounting system according to claim 7, wherein the first portion of the groove is widest at the top end of the needle mount defining an entrance.

10. The needle mounting system according to claim 7, wherein the protrusions comprise a circular surface.

11. The needle mounting system according to claim 7, further comprising a means for determining whether the needle hub is securely mounted on the needle mount.

12. The needle mounting system according to claim 7, wherein the needle mount is on an adapter top that is secured to an ampoule, or an injection device.

* * * * *